United States Patent [19]

Loeffler et al.

[11] 4,239,775
[45] Dec. 16, 1980

[54] 2-(1-METHYLPROPYN-2-YL-THIO)-PHENYL-N-METHYLCARBAMATE AND ITS USE FOR COMBATING PESTS OF THE ACARINA ORDER

[75] Inventors: Hans-Peter Loeffler, Ludwigshafen; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 66,554

[22] Filed: Aug. 15, 1979

[30] Foreign Application Priority Data

Aug. 28, 1978 [DE] Fed. Rep. of Germany ....... 2837407

[51] Int. Cl.$^3$ .................. C07C 125/067; A61K 31/27
[52] U.S. Cl. ........................................ 424/300; 560/135
[58] Field of Search ......................... 560/135; 424/300

[56] References Cited

U.S. PATENT DOCUMENTS

| | | | |
|---|---|---|---|
| 3,857,860 | 12/1974 | Kuhle et al. | 560/135 |
| 3,910,991 | 10/1975 | Nikles | 560/132 |

FOREIGN PATENT DOCUMENTS 1148107  5/1963 Fed. Rep. of Germany .
1183490 12/1964 Fed. Rep. of Germany .

OTHER PUBLICATIONS

Fukuto et al., "J. Econ. Ent.", vol. 57, (1964), pp. 10–12.

Primary Examiner—Joseph E. Evans
Attorney, Agent, or Firm—Keil & Witherspoon

[57] ABSTRACT

The compound 2-(1-methylpropyn-2-yl-thio)-phenyl-N-methylcarbamate of the formula

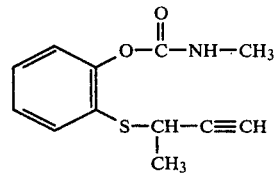

and a process for combating pests with this compound. The compound is effective on pests such as ectoparasites, and especially ticks.

2 Claims, No Drawings

2-(1-METHYLPROPYN-2-YL-THIO)-PHENYL-N-METHYLCARBAMATE AND ITS USE FOR COMBATING PESTS OF THE ACARINA ORDER

The present invention relates to the compound 2-(1-methylpropyn-2-yl-thio)-phenyl-N-methylcarbamate, pesticides containing this carbamate as active ingredient, and a process for producing this carbamate.

Insecticidally active carbamates of thiopyrocatechol have been disclosed. For instance, 2-sec-butylthiophenyl-N-methylcarbamate is effective on flies (J. Econ. Ent., 57. 10–12, 1964), 2-allylthiophenyl-N-methylcarbamate is used in particular for protecting materials against termites (German Printed Application DE-AS No. 1,148,107), and 2-propargylthiophenyl-N-methylcarbamate effectively combats caterpillars (German Printed Application DE-AS No. 1,183,490).

Furthermore, German Laid-Open Application DE-OS No. 1,962,408 discloses that 2-(1-methylpropyn-2-yl-oxy)-phenyl-N-methylcarbamate is particularly effective as an insecticide and acaricide.

We have found that 2-(1-methylpropyn-2-yl-thio)-phenyl-N-methylcarbamate of the formula

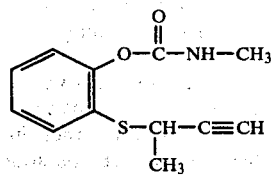

has a very good action on pests, for instance ectoparasites. In particular, the carbamate has a very good action on ticks. Surprisingly, its action is superior to that of the analogous oxygen compound 2-(1-methylpropyn-2-yl-oxy)-phenyl-N-methylcarbamate (German No. 1,962,408).

2-(1-methylpropyn-2-yl-thio)-phenyl-N-methylcarbamate may be obtained by reaction of 2-(1-methylpropyn-2-yl-thio)-phenol with methyl isocyanate, if desired in the presence of a catalyst and, if desired, in the presence of an inert organic solvent or diluent. The reaction is advantageously carried out in an inert solvent or diluent. Suitable examples are ethers, such as diethyl ether, dioxane, and tetrahydrofuran, aromatic hydrocarbons, such as benzene, toluene, and xylenes, and chlorinated aliphatic hydrocarbons, such as methylene chloride. Mixtures of these solvents may also be used.

The reaction may if desired be accelerated by catalysts conventionally used for the reaction of isocyanates with phenols, such as organic amines, e.g., trimethylamine, triethylamine, and 1,4-diazabicyclo-[2,2,2]-octane, or organic tin compounds, e.g., di-n-butyltin diacetate and di-n-butyltin dichloride. Advantageously, from 0.0001 to 0.1 mole of catalyst is added per mole of 2-(1-methylpropyn-2-yl-thio)-phenol.

Good yields of 2-(1-methylpropyn-2-yl-thio)-phenyl-N-methylcarbamate are obtained when the starting materials are employed in equimolar ratios. Generally, from 1 to 2 moles of methyl isocyanate are used per mole of 2-(1-methylpropyn-2-yl-thio)-phenol.

The reaction temperature may vary from −10° to +100° C., and is preferably from room temperature to 75° C.

To prepare the 2-(1-methylpropyn-2-yl-thio)-phenol, monothiopyrocatechol (J. Chem. Soc., 1514, 1953) is reacted with 3-chloro-1-butyne or 3-bromo-1-butyne. The reaction is preferably carried out in solvents and in the presence of equimolar amounts of a base. Examples of solvents which may be used are ethers, such as diethyl ether and dioxane, ketones, such as acetone and methyl ethyl ketone, and nitriles, such as acetonitrile. Bases which may be used are organic bases, such as triethylamine, or inorganic bases, such as potassium carbonate. It is advisable to carry out the reaction in the absence of oxygen.

The following examples illustrates the manufacture of 2-(1-methylpropyn-2-yl-thio)-phenyl-N-methylcarbamate.

EXAMPLE 1

21.2 g of 3-chloro-1-butyne is added to 25.2 g of 2-mercaptophenol in 100 ml of acetonitrile. Under a nitrogen blanket, 22 g of triethylamine is then dripped in. The mixture is stirred for about 4 hours and concentrated, and the residue is taken up in chloroform, washed 3 times, each time with 100 ml of water, and dried with sodium sulfate. The solvent is removed and the product is obtained in the form of a brown oil. Yield: 30 g.

3 drops of triethylamine and subsequently 0.12 mole of methyl isocyanate are added to 0.08 mole of 2-(1-methylpropyn-2-yl-thio)-phenol in 20 ml of diethyl ether. After the mixture has stood for 24 hours, the solvent and excess methyl isocyanate are removed and the product is purified by chromatography using silica gel, with chloroform as eluant. After removal of the solvents, there is obtained 10 g of 2-(1-methylpropyn-2-yl-thio)-phenyl-N-methylcarbamate as a yellow oil; $n_D^{20} = 1.570$.

2-(1-methylpropan-2-yl-thio)-phenyl-N-methylcarbamate is suitable for combating pests form the Acarina order.

Examples of members of this order are *Ornithodorus moubata, Ornithodorus megnini, Argas reflexus, Argas persicus, Ixodes ricinus, Ixodes persuleatus, Amblyomma americanum, Amblyomma hebraeum, Amblyomma maculatum, Hyalomma savignyi, Hyalomma mauretanicum, Dermacentor silvarum, Dermacentor albipictus, Dermacentor andersoni, Haemaphysalis cinnabarina, Thipcephalus sanguineus, Boophilus microplus, Boophilus annulatus, Tetranychus telarius, Tetranychus atlanticus, Tetranychus pacificus, Paratetranychus pilosus,* and *Bryobia praetiosa.*

The active ingredient may be applied as such, in the form of formulations, or of ready-to-use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient according to the invention.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, and water are suitable.

Aqueous formulations may be prepared from emulsion concentrates, pastes, oil dispersions or wettable powders by adding water. To prepare emulsions, pastes and oil dispersions, the active ingredient as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acids, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose, Powders, dusts and broadcasting agents may be prepared by mixing or grinding the active ingredient with a solid carrier.

Granules, e.g., coated, impregnated or homogeneous granules, may be prepared by bonding the active ingredient to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of the active ingredient.

The amount of active ingredient in the ready-to-use formulations may vary within a wide range; it is generally from 0.0001 to 10%, preferably from 0.01 to 1%.

The active ingredient may also be successfully used in the ultra-low volume method, where it is possible to apply formulations containing more than 95% of active ingredient, or even the 100% active ingredient.

Examples of formulations are given below.

I. 3 parts by weight of 2-(1-methylpropyn-2-yl-thio)-phenyl-N-methylcarbamate is intimately mixed with 97 parts by weight of particulate kaolin. A dust is obtained containing 3% by weight of the active ingredient.

II. 30 parts by weight of 2-(1-methylpropyn-2-yl-thio)-phenyl-N-methylcarbamate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of 2-(1-methylpropyn-2-yl-thio)-phenyl-N-methylcarbamate is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of 2-(1-methylpropyn-2-yl-thio)-phenyl-N-methylcarbamate is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

There may be added to the active ingredients (if desired, immediately before use (tankmix)) oils of various types, herbicides, fungicides, other insecticides, and bactericides. These agents may be added in a weight ratio of from 1:10 to 10:1.

Examples of agent which may be admixed are as follows: 1,2-dibromo-3-chloropropane, 1,3-dichloropropene, 1,3-dichloropropene+1,2-dichloropropane, 1,2-dibromoethane, 2-sec-butylphenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-0-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenylphosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethylphosphonodithioate, O,O-diethyl-[2-chloro-1-(2,4-dichlorophenyl)-vinyl]-phosphate, O,O-dimethyl-[-2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethyl-phosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbomoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-(dimethylcarbamoyl)-vinyl]-phosphate, O,O-dimethyl-O-[(1-methyl-2-chloro-2-diethylcarbamoyl)-vinyl]-phosphate, O,O-diethyl-S-(ethylthiomethyl)-phosphorodithioate, O,O-diethyl-S-](p-chlorophenylthio)-methyl]-phosphorodithioate, O,O-diethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3yl)-thionophosphate, O,S-dimethylphosphoroamidothioate, O,S-dimethyl-N-acetylphosphoramidothioate, γ-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2allyl-3methyl-cyclopenten-(2)-on-(1)-yl-(4)-DL-cis,trans-chrysanthemate, 5-benzylfuryl-(3)-methyl-DL-cis,-trans-chrysanthemate, 3-phenoxybenzyl(+)-cis,trans-2,2-dimethyl-3-(2,2-dichlorovinyl)-cycloproancarboxylate, α-cyano-3-phenoxybenzyl(+)-cis,-trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydropthalimidoethyl-DL-cis,trans-chrysanthemate, 2-methyl-5-(2-propynyl)-3-furylmethyl-chrysanthemate, and α-cyano-3-phenoxybenzyl-α-isopropyl-4-chlorophenylacetate.

EXAMPLE 2

Contact action on ticks (*Ornithodorus moubata*)

Ticks in the third larval stage are placed in paper bags which are dipped for 3 seconds in emulsions of the active ingredients. The bags are then suspended. The action on the ticks is assessed after 48 hours.

The comparative agent employed is 2-(1-methylpropyn-2yl-oxy)-phenyl-N-methylcarbamate (German Laid-Open Application DE-OS No. 1,962,408).

| Active ingredient | Active ingredient concentration in emulsion (%) | Kill rate (%) |
|---|---|---|
| according to the invention | 0.005 | 100 |
|  | 0.0025 | 80 |
| comparative agent | 0.01 | 100 |
|  | 0.005 | 80 |

We claim:

1. 2-(1-methylpropyn-2-yl-thio)-phenyl-N-methylcarbamate of the formula

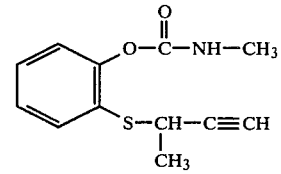

2. A process for combating pests from Acarina order, wherein 2-(1-methylpropyn-2-yl-thio)-phenyl-N-methylcarbamate is allowed to act on the pests or their habitat.

* * * * *